United States Patent [19]

Casas

[11] Patent Number: 4,548,952

[45] Date of Patent: Oct. 22, 1985

[54] 2-[(2,6-DICHLOROPHENYL)AMINO]-PHENYLACETOXYACETYL DERIVATIVES AND THERAPEUTIC COMPOSITIONS CONTAINING SAME

[75] Inventor: Antonio V. Casas, Barcelona, Spain

[73] Assignee: Prodes, S.A., San Justo Desvern, Spain

[21] Appl. No.: 590,018

[22] Filed: Mar. 15, 1984

[30] Foreign Application Priority Data

Mar. 21, 1983 [ES] Spain .................................. 520.813

[51] Int. Cl.$^4$ .................. A61K 31/24; C07C 101/447
[52] U.S. Cl. ........................................ 514/533; 560/47
[58] Field of Search ................... 560/44, 47; 424/309

[56] References Cited

PUBLICATIONS

Supplement to WHO Chronicle, vol. 38, No. 4, pp. 1-2, Oct., 1984.
Noller, C., *Chemistry of Organic Compounds*, 3rd ed., W. B. Saunders Co., Phila., (1965), pp. 185-186.
STN International, search report, Benzeneacetic acid, 2—[(2,6—dichlorophenyl)amino]—, carboxymethyl ester.

*Primary Examiner*—Natalie Trousof
*Assistant Examiner*—Bruce D. Gray
*Attorney, Agent, or Firm*—Flynn, Thiel, Boutell & Tanis

[57] ABSTRACT

2-[(2,6-Dichlorophenyl)amino]phenylacetoxyacetyl derivatives are disclosed which have anti-inflammatory and analgesic properties. A method for making the foregoing compounds is also disclosed wherein a 2-[(2,6-dichlorophenyl)amino]phenylacetic acid salt is reacted with a benzyl haloacetate.

9 Claims, No Drawings

2-[(2,6-DICHLOROPHENYL)AMINO]-PHENYLACETOXYACETYL DERIVATIVES AND THERAPEUTIC COMPOSITIONS CONTAINING SAME

The present invention relates to 2-[(2,6-dichlorophenyl)amino]phenylacetoxyacetyl derivatives of medical use having the following formula:

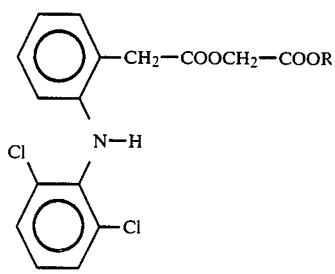

wherein R can be hydrogen, benzyl, or an organic or inorganic cation capable of forming a pharmaceutically acceptable monobasic salt.

The compounds of the present invention can be prepared by a process which comprises reacting a 2-[(2,6-dichlorophenyl)amino]phenylacetic acid salt of the formula:

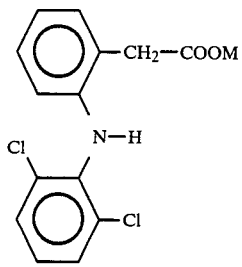

wherein M represents an alkali metal cation, preferably sodium or potassium, with a benzyl haloacetate, preferably a bromoacetate, of the formula:

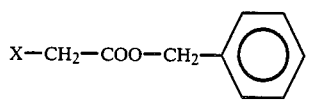

wherein X is a halogen atom. The reaction of the compounds of formulas (II) and (III) is conducted by heating the compounds (II) and (III) to 50°–150° C. in an anhydrous organic liquid medium of polar and aprotic character (for instance dimethylformamide, acetonitrile, dimethylsulphoxide, and the like) for a period which can vary from 2 to 20 hours. When R is hydrogen, preparation is completed by hydrogenation of the benzyl ester of formula (I), obtained by the former process, at a temperature of 25°–70° C. and pressure of 1–6 atmospheres, by means of the catalytic action of a transition metal, preferably Pd absorbed on carbon.

The new 2-[(2,6-dichlorophenyl)amino]-phenylacetoxyacetyl derivatives, according to the present invention, are compounds of therapeutic use with anti-inflammatory and analgesic pharmacologic properties, as shown by experimental pharmacologic data presented below. The analgesic activity of the compound (I) where R=H was determined by three known methods as follows.

(a) Test of abdominal contractions by acetic acid

This test was carried out according to the experimental model described by Koster R., Anderson, M. and De Bear, E. J. Fed. Proc., 18, 412 (1959). A suspension of the product to be tested was administered to a group of male mice through a gastric catheter half an hour before injecting the mice intraperitoneally with 0.2 ml of a 2% acetic acid solution. The number of abdominal contractions, manifested by drawing in of the rear third of the animal as a consequence of the chemical aggression incited by the acetic acid, were then counted. The compound (I) of the invention wherein R=H was tested at two dosages, with results as shown in Table 1.

TABLE 1

| No. Animals | DOSAGE | % PROTECTION (CONTROL OF CONTRACTIONS) |
|---|---|---|
| 16 | 100 mg/kg | 30.81% |
| 16 | 250 mg/kg | 67.62% |

(b) Hot plate thermal stimulus test on mice

This test is carried out according to the experimental model of Wolfe, G. and MacDonal, A. D., described in 3. Pharm. Exper. Therap. 80, 300 (1944). This test consists of administering, through a gastric catheter, a suspension of the test compound at the indicated dosages. After 30 minutes, 1 h., 1½ h. and 2 h. the determinations were made. Mice were placed onto a hot plate at a temperature of 56° C. Table 2 indicates the percentage of protection from pain afforded by the dosages of the test compound in comparison with a group of control mice to which no test compound was administered.

TABLE 2

| No. Animals | DOSAGE | % PROTECTION |
|---|---|---|
| 10 | 20 mg/kg | 22.44% |
| 10 | 40 mg/kg | 24.80% |

(c) Podolorimetric test in a rat

This test is based upon the method described by Randall, L. and Selitto, 3. Arch. Int. Pharmacodyn. 111, 409 (1957), consisting of administering the drug in a 1% carboxymethylcellulose (CMC) suspension. The test compound is administered to the rat, and 30 minutes thereafter a 20% yeast suspension is administered into the left leg of the rat and the same amount of physiologic serum is administered to the right leg of the rat. The threshold of the weight supported by both legs is determined 1 h., 2 h. and 4 h. after the administration of the yeast. Table 3 states the percentage of protection in terms of increased weight supported by the yeast-infected leg, relative to the dosage of the test compound, in comparison with a group of control rats to which no test compound was administered.

TABLE 3

| No. Animals | DOSAGE | % PROTECTION |
|---|---|---|
| 10 | 2.5 mg/kg | 32.05% |
| 10 | 10 mg/kg | 45.45% |

The anti-inflammatory activity of two compounds was studied by means of the test of the plantar carrageenin edema (C. A. Winter, Proc. Soc. Exp. Brol. Med. 111, 544–47 (1962). The method used consists of preparing homogeneous lots of albino Sprague-Dawley male rats with weights of from 180–200 gr, to which are administered, by gastric catheter, the test compound suspended in a vehicle containing 0.2% CMC and 0.1% Tween 80, sixty minutes before the production of the subplantar edema. The amount of the test compounds administered was 10 mg/kg rat body weight in all cases, and the control group received the same amount of vehicle without any test compound. Immediately after this, all the rats received via oral administration 20 ml/kg of distilled water to attain uniform hydration. 60 minutes later a 1% carrageenin solution in physiologic serum was administered subcutanaceously into the left rear leg of each rat, at a dosage of 0.1 ml/rat. The same amount of physiologic serum was then injected into the right rear leg of each rat.

The plantar amount of the left and right rear extremities of each rat was determined before the administration of the carrageenin solution, and 1, 2, 3, 4, 5 and 6 hours after the administration thereof by means of a mercury plethysmograph, Ugo Basile Model 7.100. Indomethacin was used as a sample drug for purposes of comparison. Results were calculated as percentages representing the value indicated for each area relative to the value of the areas for the control group to which were assigned the value of 100% inflammation. A complementary value, the percentage of inhibition, was also calculated from the data. The arithmetic average and standard deviation ($M \pm \sigma$) were calculated for the obtained values as to the volumes of each leg, normal or inflamed, for each animal in each group (control and treated). Table 4 shows the results obtained when the compounds (I) wherein $R=H$ and $R=CH_2-C_6H_5$ were administered according to the foregoing procedure.

TABLE 4

| PRODUCT | DOSAGE | No. Animals | % Area Relative Inflammation ($M \pm \sigma$) | Inhibition % $M \pm \sigma$ |
|---|---|---|---|---|
| CONTROL | 1.9 ml/kg | 40 | 100 | 0 |
| INDOMETHACIN | 2.5 mg/kg | 40 | 53.48 ± 7.82 | 46.52 |
| I, R = H | 3.0 mg/kg | 32 | 63.25 ± 5.88 | 33.75 |
| I, R = CH$_2$—C$_6$H$_5$ | 3.75 mg/kg | 32 | 64.04 ± 7.91 | 35.96 |

The acute toxicity of the foregoing compounds according to the present invention was studied by oral administration thereof to rats. The $LD_0$ and $LD_{50}$ values were determined, together with the limits of reliability as determined by the method of Litchfield and Wilcoxon. Table 5 below summarizes these results.

TABLE 5

| COMPOUND | $LD_{50}$ (mg/kg) | | $LD_0$ (mg/kg) |
|---|---|---|---|
| I, R = H | 120.92 | 154.06 (max) 94.91 (min) | 68.03 |
| I, R = CH$_2$—C$_6$H$_5$ | 95.31 | 130.16 (max) 69.77 (min) | 38.51 |

The subacute toxicity of the foregoing compounds was studied by oral administration thereof, by catheter, over a period of one month to groups of 120 Wistar rats of both sexes. Administration of the test compounds was carried out six days per week. The dosages used were 15 mg/kg/day, 50 mg/kg/day and 100 mg/kg/day. A group of control rats received equivalent amounts of excipient only (1% CMC suspension). The parameters studied over the course of the test were the evolution of mortality, weight change rate, food consumption, hematic, biochemical and urinary functions, as well as a histopathologic study. The results were that no harmful effects were observed, except that a high dosage of 100 mg/kg/day for the compound (I) wherein $R=H$, some cases of mortality together with blood in the excrement were observed, and the histologic study showed the presence of irritation of the gastric and/or intestinal mucous membranes.

The fetal and teratogenous toxicity of the compounds (I) wherein $R=H$ and $R=$benzyl were studied in Sprague-Dawley rats and first generation fetuses using dosages of 15, 50 and 75 mg/kg/day by oral administration. Such administration during the period of organogenesis did not produce any toxic effects on the gestating females and did not have any teratogenous effects.

The compounds (I) of the present invention can be used in human therapy. The preferred daily dosages for oral administration to human beings are 50–150 mg for the compound (I) wherein $R=H$ and 150–200 mg for the compound (I) wherein $R=CH_2-C_6H_5$. The compounds of the present invention can be formulated with conventional carriers and vehicles and administered in the form of tablets, recovered tablets, capsules, syrups and suppositories. Soluble salts of the compound (I) wherein $R=H$, such as the sodium salt, can be administered as injectable solutions.

The following are some examples of pharmaceutical compositions for administering the compounds of the present invention. The amounts given below are parts by weight unless otherwise indicated.

| | I, R = H | I, R = CH$_2$—C$_6$H$_5$ |
|---|---|---|
| Tablets: | | |
| Compound (I) | 55.6 | 63.6 |
| Lactose | 50.0 | 42.0 |
| Sodium carboxymethylcellulose | 10.0 | 10.0 |
| Magnesium stearate | 2.4 | 2.4 |
| Suspensions: | | |
| Compound (I) | 166.8 | 180.0 |
| Aerosil P-101 | 100.0 | 100.0 |
| Sorbitol 70% | 2000.0 | 2000.0 |
| Methylparaben | 7.5 | 7.5 |
| Propylparaben | 2.5 | 2.5 |
| Water c.s.p. | 150.0 | 136.8 |
| Suppositories: | | |
| Compound (I) | 75 mg. | 100 mg. |
| Stearinum mass C | 2.5 g | 2.5 g |

The following examples show illustrative methods for preparing compounds according to the present invention, but do not limit the scope of the invention.

EXAMPLE 1

Synthesis of Benzyl 2-[(2,6-dichlorophenyl)amino]phenylacetoxyacetate 50 g (0.166 moles) of sodium 2-[(2,6-dichlorophenyl)amino]phenylacetate were dissolved in 300 ml of N,N'-dimethylformamide under heating to 50° C., and 44.22 g (0.193 moles) of benzyl bromoacetate were added thereto. The resulting mixture was stirred under these conditions for eight hours. Thereafter, the reaction solvent was removed under reduced pressure and sodium salts were precipitated by adding 400 ml of ethyl ether. The ether phase was then filtered and washed three times with 100 ml of water, and then dried on sodium sulphate. The ether phase was then concentrated until an oil was obtained, and was washed twice with 100 ml of hexane. The resulting product was crystallized from the hexane/ether mixture, which did not include a first darker fraction separated in the form of an oil. There was obtained 44.1 g (70%) of benzyl 2-[(2,6-dichlorophenyl)amino]phenylacetoxy acetate in the form of white crystals having a melting point of 67°–69° C. Rf=0.73 (acetone 10/chloroform 90). Spectral data and the elemental analysis for this compound were as follows.

IR: (KBr)$_{vmax}$ 3370, 3000, 1755,1735, 1570, 1500, 1440, 1420, 1390, 1360, 1290, 1270, 1190, 1140, 770, 750, and 700 cm$^{-1}$ H$^1$NMR: (CDCl$_3$) ppm 6.5–7.4 (m,12 H, aromatic), 5.15 (s, 2 H, OC$\underline{H_2}$—Ar), 4.7 (s, 2 H, O—C$\underline{H_2}$—COO), 3.9 (s, 2 H, Br—C$\underline{H_2}$—COO).

Elemental analysis:

| | Empirical formula C$_{23}$H$_{19}$Cl$_2$NO$_4$ | | | |
|---|---|---|---|---|
| | C % | H % | Cl % | N % |
| Calculated | 62.17 | 4.31 | 15.95 | 3.15 |
| Found | 61.99 | 4.33 | 15.98 | 3.13 |

Synthesis of 2-[(2,6-dichlorophenyl)amino]phenylacetoxyacetic acid 32 g (0.072 moles) of benzyl 2-[(2,6-dichlorophenyl)amino]phenylacetoxyacetate prepared above were dissolved in 1000 ml of acetic acid, and the resulting mixture was mixed with 5 g of Pd/C 10% and then hydrogenated at a pressure of 3 atmospheres under heating to a temperature of 40° C. for a period of 10 hours. The catalyst was filtered, and the resulting solution was concentrated and then washed with toluene to remove acetic acid. The product was then recrystallized from cyclohexane, thus obtaining 13 g (50%) of 2-[(2,6-dichlorophenyl)amino]phenylacetoxyacetic acid, in the form of white crystals having a melting point of 149°–150° C., Rf=0.51 (acetone 100/acetic acid 2.5). Spectral data and elemental analysis of the product were as follows.

IR: (KBr)$_{vmax}$ 3320 (env), 1770, 1715, 1580,, 1570, 1490, 1440, 1415, 1340, 1280, 1250, 1130 (env), 1050, 1050, 960, 930, 900, 850, 770, 750, and 710 cm$^{-1}$ H$^1$NMR: (CDCl$_3$), ppm 8.6–8.9 (s, 1 H, COOH), 6.3–7.5 (m, 8 H, aromatics and N—H), 4.65 (s, 2 $\overline{\text{H}}$, COOC$\underline{H_2}$—COO) 3.9 (s, 2 H; Ar—C$\underline{H_2}$—COO).

UV spectrum λmax=275 nm., Log. ε=4.14 (ETOH)

Elemental Analysis:

| | Empirical formula C$_{16}$H$_{13}$Cl$_2$NO$_4$ | | | |
|---|---|---|---|---|
| | C % | H % | Cl % | N % |
| Calculated | 54.28 | 3.69 | 20.00 | 3.95 |
| Found | 54.11 | 3.72 | 20.02 | 3.97 |

EXAMPLE 2

Synthesis of Benzyl 2-[(2,6-dichlorophenyl)amino]phenylacetoxyacetate 50 g (0.166 moles) of sodium 2-[(2,6-dichlorophenyl)amino]phenylacetate were dissolved in 200 ml of N,N'-dimethylformamide under heating to 50° C., and 41.620 g (0.181 moles) of benzyl bromoacetate were added thereto. Under these conditions stirring was continued for 3 hours. Upon completion of the reaction, the solvent was removed at reduced pressure and the sodium salts were precipitated with addition of 400 ml of ether. The solution was then filtered and the ether phase was washed three times with 100 ml of water and dried on sodium sulphate. The resulting product was concentrated until an oil was obtained, which oil was washed twice with 100 ml of hexane and then crystallized with methanol, thus obtaining 45.28 (61%) of 2-[(2,6-dichlorophenyl)amino]phenylacetoxy acetate.

Synthesis of 2-[(2,6-dichlorophenyl)amino]phenylacetoxyacetic acid 45.28 g (0.102 moles) of benzyl 2-[(2,6-dichlorophenyl)amino]phenylacetoxyacetate prepared above were dissolved in 1500 ml of ethyl acetate, and the resulting mixture was mixed with 7 g of Pd/C 10% and then hydrogenated at atmospheric pressure for 14 hours. The solution was then filtered, concentrated and crystallized, thereby obtaining 23.51 g (65%) of 2-[(2,6-dichlorophenyl)amino]phenylacetoxyacetic acid.

The embodiments of the invention in which an exclusive property or privilege is claimed are defined as follows:

1. A compound of the formula:

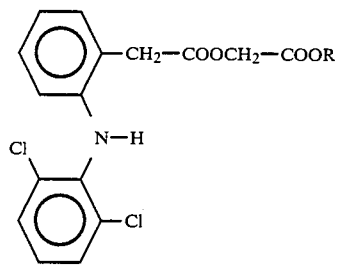

wherein R is hydrogen, benzyl, or an organic or inorganic cation capable of forming a therapeutically acceptable monobasic salt.

2. A compound according to claim 1 which is benzyl 2-[(2,6-dichlorophenyl)amino]phenylacetoxyacetate.

3. A compound according to claim 1 which is 2-[(2,6-dichlorophenyl)amino]phenylacetoxyacetic acid.

4. A compound according to claim 1, wherein R is sodium.

5. A pharmaceutical composition for treatment of inflammation and pain comprising a therapeutically effective amount of a compound as claimed in claim 1, in combination with a pharmaceutically acceptable carrier, diluent, or vehicle.

6. A method of treating a subject suffering from pain which comprises administering to said subject a therapeutically effective amount of a pharmaceutical composition according to claim 5.

7. A method of treating a subject suffering from inflammation which comprises administering to said subject a therapeutically effective amount of a pharmaceutical composition according to claim 5.

8. A process for the preparation of a compound of the formula:

which comprises hydrogenating a compound of the formula:

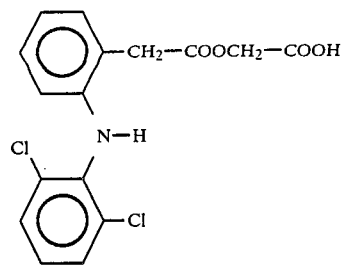
(IV)

obtained by reacting a compound having the formula:

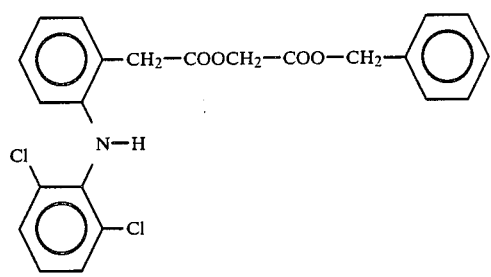
(I)

wherein M represents a cation, with a compound of the formula:

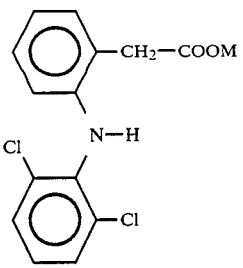
(II)

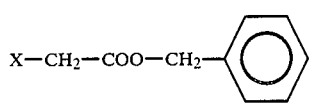
(III)

wherein X is a halogen, under heating in an anhydrous organic liquid medium of polar and aprotic character, in the presence of an effective amount of a hydrogenation catalyst.

9. A process as claimed in claim 8, wherein said catalyst comprises palladium deposited on carbon.

* * * * *